United States Patent
Heuer et al.

(10) Patent No.: US 7,183,419 B2
(45) Date of Patent: Feb. 27, 2007

(54) 3,4-DIOXYTHIOPHENE DERIVATIVES

(75) Inventors: Helmut-Werner Heuer, Krefeld (DE); Rolf Wehrmann, Krefeld (DE)

(73) Assignee: H.C. Starck GmbH & Co. KG, Goslar (DE)

( * ) Notice: Subject to any disclaimer, the term of this patent is extended or adjusted under 35 U.S.C. 154(b) by 288 days.

(21) Appl. No.: 11/011,515

(22) Filed: Dec. 14, 2004

(65) Prior Publication Data

US 2005/0137407 A1    Jun. 23, 2005

(30) Foreign Application Priority Data

Dec. 19, 2003 (DE) ................................ 103 59 796

(51) Int. Cl.
*C07D 409/00* (2006.01)

(52) U.S. Cl. ..................................................... 549/60
(58) Field of Classification Search ................... 549/60
See application file for complete search history.

(56) References Cited

U.S. PATENT DOCUMENTS

| | | | |
|---|---|---|---|
| 4,072,693 A | 2/1978 | Reinhoudt et al. ........... | 260/338 |
| 4,152,335 A | 5/1979 | Reinhoudt et al. ........... | 260/338 |
| 5,035,926 A | 7/1991 | Jonas et al. ............... | 427/393.1 |
| 5,111,327 A | 5/1992 | Blohm et al. ............... | 526/256 |
| 6,130,339 A * | 10/2000 | Tan et al. ..................... | 549/50 |
| 6,683,709 B2 * | 1/2004 | Mann et al. ................. | 359/241 |
| 6,869,696 B2 * | 3/2005 | Richter et al. ............... | 428/690 |

OTHER PUBLICATIONS

S. Scheib et al: "Synthesis and characterization of oligo- and crown ether-substituted polythiophenes—a comparative study" Journal of Materials Chemistry, Bd. 9, Nr. 9, 1999, Seiten 2139-2150, XP002317502.

T. Sone et al: "Synthesis and reductive desulfurization of crown ethers containing thiophene subunit" Bulletin of the Chemical Society of Japan, Bd. 62, Nr. 3, 1989, Seiten 838-844, XP002317503.

* cited by examiner

*Primary Examiner*—Deborah C. Lambkin
(74) *Attorney, Agent, or Firm*—Connolly Bove Lodge & Hutz LLP

(57) ABSTRACT

A process for the production of 3,4-dioxythiophene compounds represented by the following formula (I),

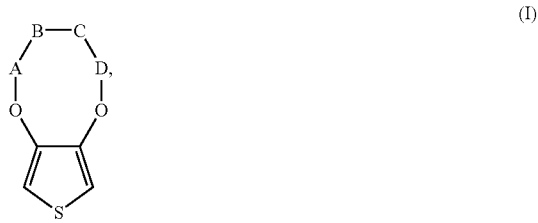

is described. In formula (I) A, B, C and D in each case independently denote a bond, optionally substituted alkylene, optionally substituted cycloalkylene, optionally substituted arylene or $(O-(CR^1R^2)_m)_x$, where $R^1$ and $R^2$ in each case mutually independently denote hydrogen or optionally substituted alkyl, m denotes an integer from 1 to 10 and x denotes an integer from 1 to 10, provided that at least one of the units A, B, C or D does not denote a bond. The process involves reacting a 3,4-dihydroxythiophene or the alkali metal salt thereof with the following compound, TosO-A-B-C-D-OTos, thus forming an intermediate 3,4-dioxythiophene diester. The intermediate 3,4-dioxythiophene diester is saponified, thus forming an intermediate 3,4-dioxythiophene dicarboxylic acid, which is then decarboxylated, thereby forming the 3,4-dioxythiophene compound represented by formula-(I).

9 Claims, No Drawings

3,4-DIOXYTHIOPHENE DERIVATIVES

CROSS REFERENCE TO RELATED PATENT APPLICATION

The present patent application claims the right of priority under 35 U.S.C. §119 (a)–(d) of German Patent Application No. 103 59 796.4, filed Dec. 19, 2003.

FIELD OF THE INVENTION

The invention relates to a process for the production of 3,4-dioxythiophene derivatives by reacting ditosylates or ditriflates with suitable 3,4-dihydroxythiophenes or the alkali metal salts thereof. The invention furthermore relates to compounds obtainable in said matter, which may be used as building blocks for π-conjugated polymers.

BACKGROUND OF THE INVENTION

Compounds of the class of π-conjugated polymers have been the subject of numerous publications in recent decades. They are also known as conductive polymers or synthetic metals.

Due to the considerable delocalisation of the π-electrons along the main chain, these polymers exhibit interesting (nonlinear) optical properties and, once oxidised or reduced, are good electrical conductors. As a consequence, these compounds may be used in various practical applications, such as for example in data storage, optical signal processing, the suppression of electromagnetic interference (EMI) and solar energy conversion, as well as in rechargeable batteries, light-emitting diodes, field effect transistors, printed circuit boards, sensors, capacitors, electrochromic devices and antistatic materials.

Examples of known π-conjugated polymers are polypyrroles, polythiophenes, polyanilines, polyacetylenes, polyphenylenes and poly(p-phenylene vinylenes). One particularly important and widely industrially used polythiophene is poly(ethylene 3,4-dioxythiophene) (Baytron®P), which, in its oxidised form, exhibits very high levels of conductivity.

However, other derivatives of poly(3,4-dioxythiophene) are also of interest, since, by suitable selection of the residues attached to the two oxygen atoms of the 3,4-dioxythiophene, it is possible purposefully to adjust, for example, the polymer's solubility in organic solvents, its electrochemical properties and its conductivity.

A problematic issue associated with the use of such poly(3,4-dioxythiophene) derivatives is that the thiophene monomers required are often only available by means of complex, low-yielding syntheses or are completely unobtainable by means of usual methods.

SUMMARY OF THE INVENTION

The object of the present invention is accordingly to provide a simple synthesis for 3,4-dioxythiophene derivatives which may be used in the widest possible range of applications and by means of which synthesis the desired products may be obtained in good yields from readily available raw materials.

It has now been found that that numerous 3,4-dioxythiophene derivatives may straightforwardly be produced by reacting readily available 2,5-dicarbalkoxy-3,4-dihydroxythiophenes with ditosylates or ditriflates and then performing hydrolysis and decarboxylation. This process is in particular distinguished in that numerous ditosylates are available and may be used as they are very straightforwardly obtainable from the corresponding diols by reaction with p-toluenesulfonic acid.

The present invention accordingly provides a process for the production of compounds of the formula (I)

wherein
A, B, C and D in each case mutually independently denote a bond, optionally substituted alkylene, optionally substituted cycloalkylene, optionally substituted arylene or (—O—(CR$^1$R$^2$)$_m$—)$_x$, in particular optionally substituted cycloalkylene, optionally substituted arylene or (—O—(CR$^1$R$^2$)$_m$—)$_x$, where
R$^1$ and R$^2$ are in each case mutually independently hydrogen or optionally substituted alkyl, preferably optionally substituted C$_1$–C$_6$-alkyl,
m is an integer from 1 to 10 and
x is an integer from 1 to 10,
providing that at least one of the units A, B, C or D does not denote a bond,
said process comprising,
(i) reacting a compound represented by the following formula (II),

wherein
A, B, C and D are each as described with regard to formula (I), and
Tos denotes a member selected from the group consisting of p-toluenesulfonyl and trifluoromethanesulfonyl,
with a thiophene represented by the following formula (III),

wherein,
R denotes C$_1$–C$_{18}$ alkyl, and
m denotes H, Li, Na or K,
thereby forming an intermediate 3,4-dioxythiophene diester,
(ii) saponifying the intermediate 3,4-dioxythiophene diester, thereby forming an intermediate 3,4-dioxythiophene dicarboxylic acid, and
(iii) decarboxylating said intermediate 3,4-dioxythiophene dicarboxylic acid, thereby forming the compound represented by formula (I).

Unless otherwise indicated, all numbers or expressions, such as those expressing reactions conditions, quantities of ingredients, ranges, etc. used in the specification and claims are understood as modified in all instances by the term "about."

The term "substituted" above and below means in particular if not otherwise indicated halogen substituted. Particularly preferred "substituted" means a substitution with F, Cl or Br in particular with F.

DETAILED DESCRIPTION OF THE INVENTION

A, B, C and D of formula (I) may in each case have a plurality of different meanings and so jointly form the most varied units, such that the process according to the invention is extremely versatile.

For example, A, B, C and D may jointly denote $-(CR^3R^4)_n-(CH_2)_o-(CR^5R^6)_p-$ or $-(CH_2)_q-(CR^7R^8)_r-(CH_2)_s-$, wherein $R^3$, $R^4$, $R^5$, $R^6$, $R^7$ and $R^8$ in each case mutually independently denote hydrogen, halogen or optionally substituted $C_1-C_{10}$ alkyl and n, o, p, q, r and s in each case mutually independently denote an integer from 1 to 10.

$R^3$, $R^4$, $R^5$, $R^6$, $R^7$ and $R^8$ preferably in each case mutually independently denote hydrogen or $C_1-C_6$ alkyl.

n, o, p, q, r and s preferably in each case mutually independently denote an integer from 1 to 5, particularly preferably from 1 to 3.

A, B, C and D may also jointly denote optionally substituted $C_6-C_8$ cycloalkylene, for example cyclohexylene or cyclooctylene.

In a preferred embodiment, A, B, C and D jointly denote $-((CR^9R^{10})_a-O)_b-(CR^{11}R^{12})_c-$, wherein $R^9$, $R^{10}$, $R^{11}$ and $R^{12}$ in each case mutually independently denote hydrogen or optionally substituted $C_1-C_{10}$ alkyl, a and c in each case mutually independently denote an integer from 1 to 10 and b denotes an integer from 1 to 8.

$R^9$, $R^{10}$, $R^{11}$ and $R^{12}$ preferably in each case mutually independently denote hydrogen or $C_1-C_6$ alkyl, in particular $R^9$, $R^{10}$, $R^{11}$ and $R^{12}$ preferably in each case denote hydrogen.

a and c preferably in each case mutually independently denote an integer from 1 to 4, in particular preferably 2 b preferably denotes 1 or 2.

The advantage of the process according to the invention is, that the process does not involve the use of phase transfer catalysts e.g. such as quarternary ammonium salts.

The phase transfer catalysts are typically expensive compounds.

After reaction they have to be removed from the process mixture by additional washing steps with watery solutions.

The removal of waste water containing phase transfer catalysts is extensive and costly.

A preferred embodiment of the new process therefore works without the presence of phase transfer catalysts or similar catalysts.

In a further particular embodiment of the process according to the invention, A, B, C and D jointly form a unit which contains at least one aromatic ring, preferably phenylene or naphthylene.

A, B, C and D preferably jointly denote a unit of the formula (IV)

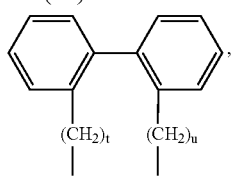

(IV)

wherein t and u in each case mutually independently denote an integer from 0 to 5 and further aromatic ring systems may be fused onto the phenyl rings. In the latter case, the biphenyl unit is preferably replaced by a binaphthyl unit.

In a further preferred embodiment, A, B, C and D jointly denote $-((CH_2)_v-X-)_y-Ar-(X-(CH_2)_w)_z-$, wherein X means a bond or oxygen and Ar means optionally substituted phenylene or optionally substituted naphthylene, and v and w in each case mutually independently denote an integer from 1 to 5 and y and z in each case mutually independently denote an integer from 1 to 10.

According to the invention, in the first reaction step a ditosylate or ditriflate is reacted with a thiophene of the formula (III)

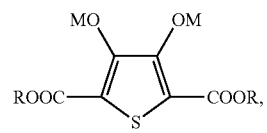

(III)

wherein

R denotes $C_1-C_{18}$ alkyl and

M denotes H, Li, Na or K.

R preferably denotes $C_1-C_{10}$ alkyl, in particular preferably methyl, ethyl or n-propyl, very particularly preferably methyl.

M preferably means hydrogen.

The reaction of the thiophene of the formula III with the desired ditosylate or ditriflate of the formula II may, for example, be performed at standard pressure in dipolar, aprotic solvents in the presence of a base such as for example potassium carbonate.

The reaction preferably proceeds under a protective gas atmosphere, for example under Ar or $N_2$.

Suitable solvents are, for example, N-methyl-2-pyrrolidone (NMP), dimethylformamide, dimethylacetamide, dimethyl sulfoxide or high-boiling ketones. N-Methyl-2-pyrrolidone is preferably used as solvent.

The reaction may, for example, be performed at a temperature of 80 to 160° C., preferably of 90 to 120° C.

Saponification and decarboxylation are then performed.

Saponification may proceed under generally conventional conditions for such a reaction. For example, heating may be performed in dilute sodium or potassium hydroxide solution, followed by neutralisation with hydrochloric or sulfuric acid.

Acidification may then follow. Acidification may, for example, proceed by addition of acids, in particular acetic acid, at temperatures of 0 to 60° C. The acid is preferably added in a quantity such that a pH value of 5–6 is established at the reaction temperature.

The subsequent decarboxylation may also be performed in a manner known per se. For example, after the saponification and optional acidification, the compound to be decarboxylated is heated to elevated temperatures, for example 160 to 200° C., in ethanolamine or in a dipolar, aprotic solvent such as dimethylacetamide or dimethyl sulfoxide, in the presence of a catalyst such as basic copper carbonate or copper chromite/quinoline.

The most varied 3,4-dioxythiophene derivatives may be obtained-using the process according to the invention. Some compounds of the formula I, in which A, B, C and D jointly form a unit which contains at least one aromatic ring, preferably benzylene or naphthylene, have not hitherto been available and are thus likewise provided by the invention.

The invention accordingly also relates to compounds of the formula (I)

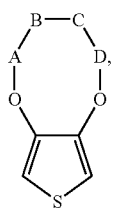

wherein A, B, C and D jointly denote a unit of the formula (IV)

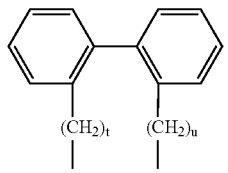

wherein t and u in each case mutually independently denote an integer from 0 to 5 and further aromatic ring systems may be fused onto the phenyl rings.

The invention also relates to compounds of the formula (I)

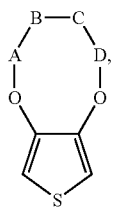

wherein A, B, C and D jointly denote —$((CH_2)_v$—X—$)_y$—Ar—$(X$—$(CH_2)_w)_z$—, wherein
X means a bond or oxygen and
Ar means optionally substituted phenylene or optionally substituted naphthylene, and
v and w in each case mutually independently denote an integer from 1 to 5 and
y and z in each case mutually independently denote an integer from 1 to 10.

The 3,4-dioxythiophene derivatives produced according to the invention may be converted in per se known manner into the corresponding oligomers and polymers, which have numerous applications.

It is possible here not only for just one compound of the formula I to be used as the monomer, but also a mixture of different compounds which fall within the definition of formula I. It is furthermore possible, apart from one or more compounds of the formula I, also to add further thiophene derivatives as monomers, in particular 3,4-ethylenedioxythiophene, which is commercially available under the name Baytron® M.

Polymerisation proceeds in accordance with the procedure used to polymerise known thiophene derivatives. It may, for example, proceed oxidatively with oxidising agents such as iron(III) chloride or other iron(III) salts, $H_2O_2$, sodium or potassium peroxydisulfate, potassium dichromate, potassium permanganate, or electrochemically.

The invention is illustrated in greater detail below by Examples, which are intended to elucidate the principle of the invention without constituting a limitation thereof.

EXAMPLES

Example 1

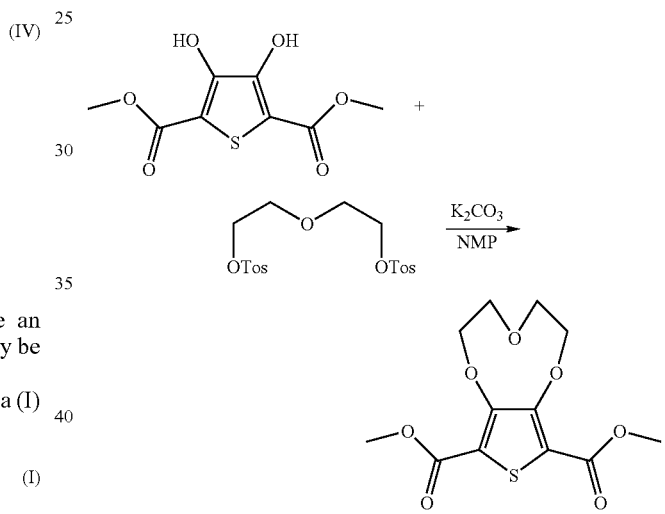

30.0 g (0.13 mol) of 3,4-dihydroxythiophene 1,2-dimethyl ester (Bayer AG, Leverkusen) and 53.88 g (0.13 mol) of diethylene glycol (p-toluenesulfonate) (Aldrich) were stirred for 18 hours at 100° C. with 44.22 g (0.32 mol) of potassium carbonate in 1500 ml of N-methylpyrrolidone (NMP). The reaction batch was combined with water and methylene chloride for working up and washed to neutrality. The organic phase was separated and dried with sodium sulfate. After evaporation of the organic phase and drying, a beige brown crude product was obtained containing as its main component the desired product with a mass of 302 (GC-MS analysis).

The crude product was purified- by recrystallisation in toluene. 10.05 g (25.6% of theoretical) of a light beige coloured solid were obtained.

The free thiophene compound may be liberated in known manner by ester cleavage (saponification and acidification) and subsequent decarboxylation, for example in a manner similar to U.S. Pat. No. 5,111,327 and EP 339 340 B1.

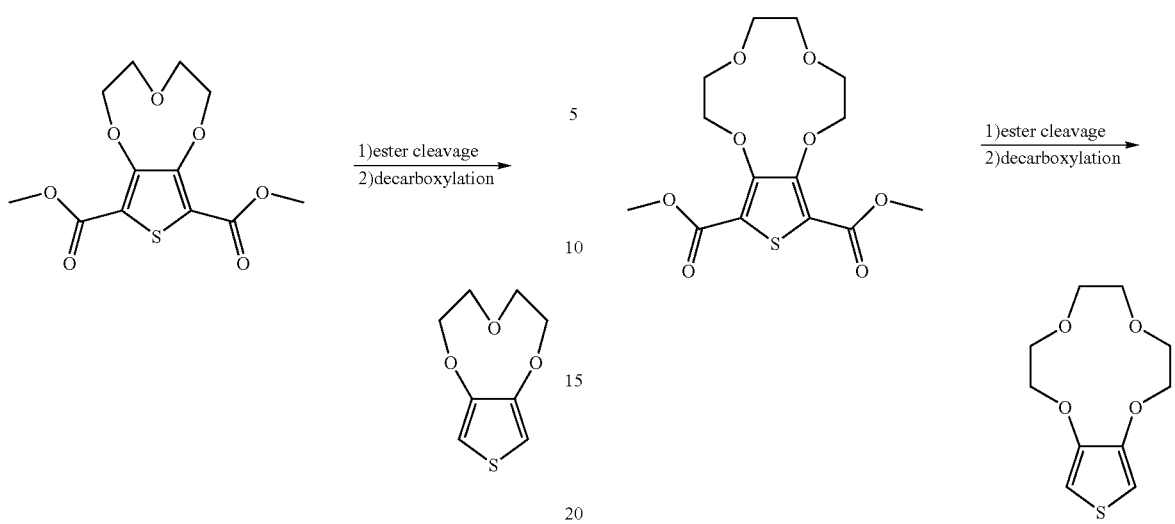

Example 2

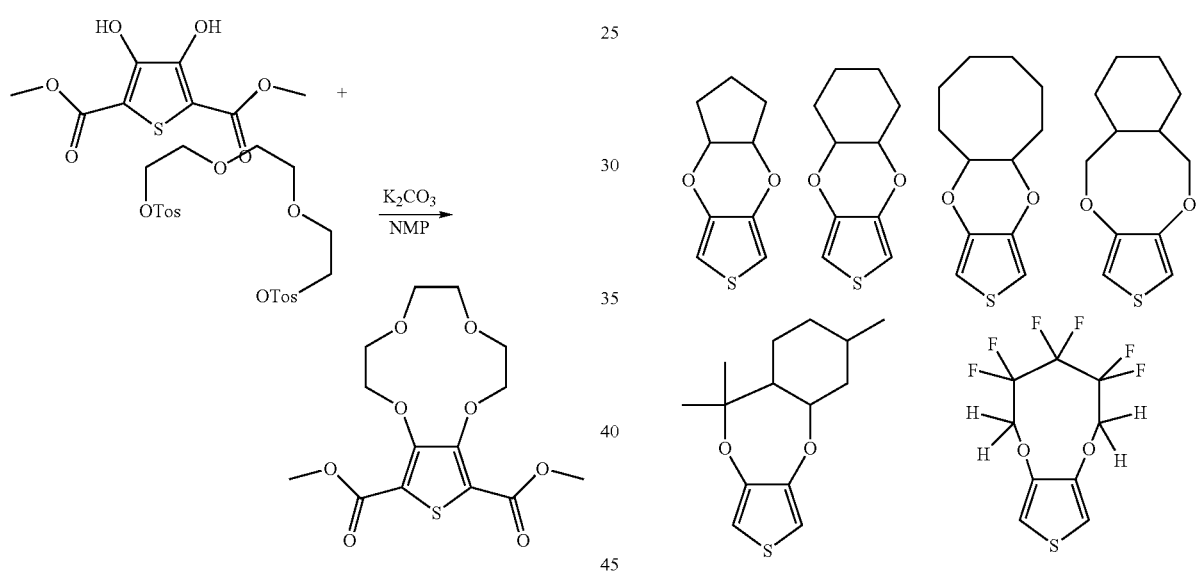

22.32 g (0.096 mol) of 3,4-dihydroxythiophene 1,2-dimethyl ester (Bayer AG, Leverkusen) and 45.85 g (0.1 mol) of triethylene glycol (p-toluenesulfonate) (Aldrich) were stirred for 18 hours at 100° C. with 34.55 g (0.25 mol) of potassium carbonate in 1500 ml of N-methylpyrrolidone. The reaction batch was combined with water and methylene chloride for working up and washed to neutrality. The organic phase was separated and dried with sodium sulfate. After evaporation of the organic phase and drying, a beige brown crude product was obtained which, on the basis of mass spectroscopy (GC-MS), had a molecular peak of a mass of 346 as the main component.

The crude product was purified by recrystallisation in methanol. 13.7 g (41.2% of theoretical) of a beige solid were obtained.

The free thiophene compound may again be liberated in known manner by ester cleavage (saponification and acidification) and subsequent decarboxylation, for example in a manner similar to U.S. Pat. No. 5,111,327 and EP 339340 B1.

The following compounds are obtainable in a similar manner:

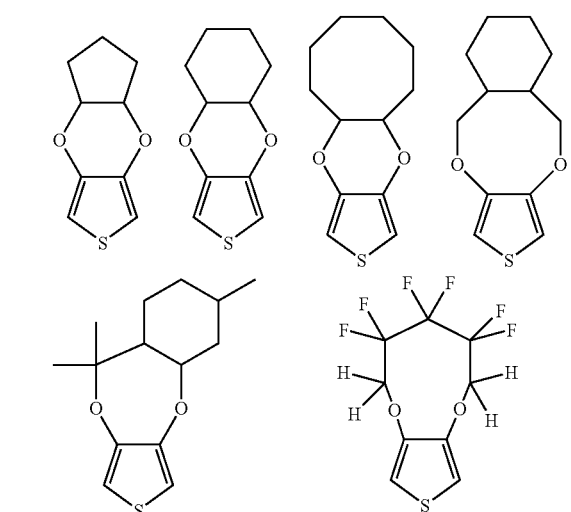

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing compounds represented by the following formula (I),

wherein,

A, B, C and D in each case independently denote a member selected from the group consisting of a bond, alkylene, substituted alkylene, cycloalkylene, substituted cycloalkylene, arylene, substituted arylene and $(-O-(CR^1R^2)_m)_x$, wherein $R^1$ and $R^2$ in each case are independently selected from the group consisting of hydrogen, alkyl, and substituted alkyl, m is an integer from 1 to 10 and x is an integer from 1 to 10, provided that at least one of the units A, B, C or D is other than a bond, said process comprising, (i) reacting a compound represented by the following formula (II),

wherein

A, B, C and D are each as described with regard to formula (I), and

Tos denotes a member selected from the group consisting of p-toluenesulfonyl and trifluoromethanesulfonyl, with a thiophene represented by the following formula (III),

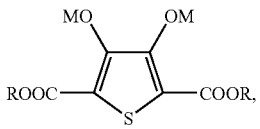

wherein,

R denotes $C_1$–$C_{18}$ alkyl, and m denotes H, Li, Na or K, thereby forming an intermediate 3,4-dioxythiophene diester, (ii) saponifying the intermediate 3,4-dioxythiophene diester, thereby forming an intermediate 3,4-dioxythiophene dicarboxylic acid, and (iii) decarboxylating said intermediate 3,4-dioxythiophene dicarboxylic acid, thereby forming the compound represented by formula (I).

2. The process of claim 1 wherein A, B, C and D together jointly denote

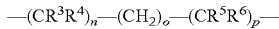

or

wherein $R^3$, $R^4$, $R^5$, $R^6$, $R^7$ and $R^8$ in each case independently denote a member selected from the group consisting of hydrogen, halogen, $C_1$–$C_{10}$ alkyl and substituted $C_1$–$C_{10}$ alkyl, and n, o, p, q, r and s in each case independently denote an integer from 1 to 10.

3. The process of claim 1 wherein A, B, C and D together jointly denote a $C_6$–$C_8$ cycloalkylene.

4. The process of claim 1 wherein A, B, C and D together jointly denote a unit represented by the following formula (IV),

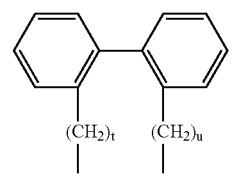

wherein, t and u in each case independently denote an integer from 0 to 5, and further aromatic ring systems may be fused onto the phenyl rings.

5. The process of claim 1 wherein A, B, C and D jointly denote

wherein

X is a bond or oxygen and

Ar denotes a member selected from the group consisting of phenylene, substituted phenylene, naphthylene and substituted naphthylene, v and w in each case independently denote an integer from 1 to 5, and y and z in each case independently denote an integer from 1 to 10.

6. The process of claim 1 wherein A, B, C and D together jointly denote,

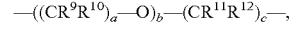

wherein $R^9$, $R^{10}$, $R^{11}$ and $R^{12}$ in each case independently denote a member selected from the group consisting of hydrogen, $C_1$–$C_{10}$ alkyl and substituted $C_1$–$C_{10}$ alkyl, a and c in each case independently denote an integer from 1 to 10, and b denotes an integer from 1 to 8.

7. The process of claim 1 wherein R denotes a member selected from the group consisting of methyl, ethyl and n-propyl.

8. A compound represented the following formula (I),

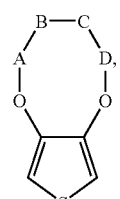

wherein,

A, B, C and D together jointly denote a unit of the formula (IV),

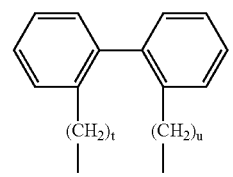

wherein, t and u in each case independently denote an integer from 0 to 5, and further aromatic ring systems may be fused onto the phenyl rings.

9. A compound represented by the following formula (I),

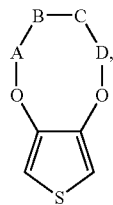

(I)

wherein,

A, B, C and D together jointly denote

—((CH$_2$)$_v$—X—)$_y$—Ar—(X—(CH$_2$)$_w$)$_z$—, wherein,

X denotes a bond or oxygen and

Ar denotes a member selected from the group consisting essentially of phenylene, substituted phenylene, naphthylene and substituted naphthylene, v and w in each case independently denote an integer from 1 to 5, and y and z in each case independently denote an integer from 1 to 10.

* * * * *